United States Patent
Bey et al.

(10) Patent No.: US 9,295,971 B2
(45) Date of Patent: *Mar. 29, 2016

(54) APPARATUS AND PROCESS FOR THE CONTINUOUS REACTION OF LIQUIDS WITH GASES

(71) Applicant: BASF SE, Ludwigshafen (DE)

(72) Inventors: Oliver Bey, Niederkirchen (DE); Andreas Raichle, Ludwigshafen (DE); Hartmut Riechers, Singapore (SG); Roland Mueller, Limburgerhof (DE); Wolfgang Mackenroth, Bad Duerkheim (DE); Peter Zehner, Weisenheim am Berg (DE)

(73) Assignee: BASF SE, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/147,805

(22) Filed: Jan. 6, 2014

(65) Prior Publication Data

US 2014/0200370 A1   Jul. 17, 2014

Related U.S. Application Data

(60) Provisional application No. 61/751,267, filed on Jan. 11, 2013.

(51) Int. Cl.
| | |
|---|---|
| *B01J 19/18* | (2006.01) |
| *B01J 19/26* | (2006.01) |
| *C07C 209/36* | (2006.01) |
| *B01J 8/22* | (2006.01) |

(Continued)

(52) U.S. Cl.
CPC ............. *B01J 19/26* (2013.01); *B01J 4/002* (2013.01); *B01J 8/006* (2013.01); *B01J 8/226* (2013.01); *B01J 8/228* (2013.01); *B01J 10/00* (2013.01); *B01J 19/246* (2013.01); *B01J 19/2465* (2013.01); *C07C 209/36* (2013.01); *B01J 2208/00132* (2013.01); *B01J 2208/00902* (2013.01); *B01J 2219/00081* (2013.01)

(58) Field of Classification Search
None
See application file for complete search history.

(56) References Cited

U.S. PATENT DOCUMENTS

| 6,838,061 B1 | 1/2005 | Berg et al. |
| 8,637,712 B2 | 1/2014 | Allardt et al. |

(Continued)

FOREIGN PATENT DOCUMENTS

| DE | 198 54 637 A1 | 5/2000 |
| DE | 10 2008 041 652 A1 | 3/2010 |

(Continued)

OTHER PUBLICATIONS

U.S. Appl. No. 14/147,793, filed Jan. 6, 2014, Bey, et al.

(Continued)

*Primary Examiner* — Clinton Brooks
(74) *Attorney, Agent, or Firm* — Oblon, McClelland, Maier & Neustadt, L.L.P.

(57) ABSTRACT

The present invention relates to an apparatus of the loop Venturi reactor type for the continuous reaction of liquids with gases, in particular for hydrogenations, oxidations or acetylations, e.g. for the preparation of toluenediamine by hydrogenation of dinitrotoluene, and a process for the continuous reaction of liquid reactants with gaseous reactants in the apparatus. Here, the cooling medium surrounds the tubes of the heat exchanger of the apparatus of the invention whereas the reaction takes place in the tubes.

21 Claims, 4 Drawing Sheets

(51) Int. Cl.
  *B01J 10/00* (2006.01)
  *B01J 19/24* (2006.01)
  *B01J 4/00* (2006.01)
  *B01J 8/00* (2006.01)

(56) References Cited

U.S. PATENT DOCUMENTS

| | | | |
|---|---|---|---|
| 2011/0144391 A1* | 6/2011 | Becker et al. | 568/420 |
| 2011/0275858 A1 | 11/2011 | Tsou et al. | |
| 2012/0238779 A1 | 9/2012 | Waters et al. | |
| 2013/0211141 A1 | 8/2013 | Raichle et al. | |
| 2014/0200351 A1* | 7/2014 | Bey et al. | 546/307 |
| 2014/0200369 A1* | 7/2014 | Bey et al. | 564/305 |

FOREIGN PATENT DOCUMENTS

| | | |
|---|---|---|
| EP | 0 034 739 A2 | 9/1981 |
| EP | 0 634 391 A1 | 1/1995 |
| EP | 1 140 349 | 10/2001 |
| EP | 1 161 297 | 12/2001 |
| EP | 1 165 231 | 1/2002 |
| GB | 1013888 | 12/1965 |
| WO | WO 00/30743 | 6/2000 |
| WO | WO 00/35852 | 6/2000 |
| WO | WO 00/51727 | 9/2000 |
| WO | WO 00/51728 | 9/2000 |
| WO | WO 2005/037768 A1 | 4/2005 |
| WO | WO 2008/138784 A1 | 11/2008 |
| WO | WO 2008/145179 A1 | 12/2008 |
| WO | WO 2010/076251 A1 | 7/2010 |
| WO | WO 2010/125025 A1 | 11/2010 |
| WO | WO 2011/144481 A1 | 11/2011 |
| WO | WO 2012/104254 A1 | 8/2012 |
| WO | WO 2012/123469 A1 | 9/2012 |
| WO | WO 2013/117622 A1 | 8/2013 |

OTHER PUBLICATIONS

U.S. Appl. No. 14/147,823, filed Jan. 6, 2014, Bey, et al.
Search Report issued Jun. 26, 2013 in European Application No. 13150903.6 (With English Translation of Category of Cited Documents).

* cited by examiner

APPARATUS AND PROCESS FOR THE CONTINUOUS REACTION OF LIQUIDS WITH GASES

The present invention relates to an apparatus of the loop Venturi reactor type for the continuous reaction of liquids with gases, in particular for hydrogenations, oxidations or acetylations, e.g. for the preparation of toluenediamine by hydrogenation of dinitrotoluene, and a process for the continuous reaction of liquid reactants with gaseous reactants in the apparatus. Here, the cooling medium surrounds the tubes of the heat exchanger of the apparatus of the invention whereas the reaction takes place in the tubes.

In many chemical processes, gas-liquid mass transfer and the heat removal performance are the rate-determining steps. Thus, in the industrially widespread preparation of aromatic monoamines and/or polyamines by reaction of the corresponding nitro compounds with hydrogen, a considerable quantity of heat is liberated. The same applies to many other hydrogenations, oxidations or acetylations. Measures for improving the heat removal performance are known per se from the prior art.

EP-A-634 391 describes a process for the hydrogenation of aromatic polynitro compounds, in which a loop Venturi reactor having an ejector (loop reactor with Venturi nozzle) is used. The way in which the process is carried out is based on specific conditions such as the precise recirculation volume ratio, the energy input, a precisely set hydrogen volume flow, by means of which, firstly, by-products are to be avoided and, secondly, the heat liberated can be utilized for steam generation. In this process, the arrangement of a heat exchanger for removing the heat of reaction outside the loop reactor, in the ejector and in the reactor can lead to local overheating with immediate commencement of secondary reactions such as ring hydrogenations, hydrogenolytic cleavages and formation of high molecular weight, tar-like products which occupy the catalyst surface. In addition, pure bubble column characteristics in respect of the flow and residence time behavior are established in the reactor volume outside the ejector due to the random occurrence of small- and large-volume eddies having a comparatively low heat transfer performance. A significant improvement in the hydrogenation yield, the hydrogenation selectivity and the space-time yield is thus not really achieved in this process. In addition, the pump circulation of the entire reaction mixture subjects the catalyst to strong mechanical stresses which in turn leads to a reduced operating life of the catalyst.

As a reactor which is particularly suitable for removing the heat of reaction, a reactor having internal and external circulatory flow (known as internal and external loop), which is configured as a vertically upright apparatus with a driving jet nozzle at its upper end through which the reaction mixture taken off from the bottom of the reactor is, via the external loop, injected into the upper region of the reactor and subsequently flows into a central plug-in tube arranged in the longitudinal direction of the reactor, flows through this from the top downward and once again flows upward in an internal loop motion outside the plug-in tube, has therefore been proposed in WO 00/35852. Field tubes in the interior of the reactor are proposed for removal of the heat of reaction.

Field tube heat exchangers are, as is known, heat exchangers which have a bundle of parallel double-walled tubes, with the ends of the outer tubes projecting into the reactor space being closed and the corresponding ends of the inner tubes being opened so that the cooling medium flows via a feed space arranged outside the reactor space into the inner tubes and flows out via the space between inner and outer tubes and also a discharge space. They are characterized by a high ratio of heat transfer area to volume of the reaction space and are thus particularly suitable for removal of the heat of reaction liberated.

EP-A 1140349 discloses a reactor for gas-liquid or gas-liquid-solid reactions having a tall-cylindrical shape and a downward-directed jet nozzle, via which the starting materials and the reaction mixture are introduced, arranged in the upper region of the reactor and an offtake in the lower region of the reactor, via which the reaction mixture is taken off and conveyed via an external circuit by means of a pump back to the jet nozzle. A concentric guide tube which extends essentially over the entire length of the reactor with the exception of the ends of the reactor and has a cross-sectional area in the range from one tenth to half of the cross-sectional area of the reactor is arranged in the reactor.

It has, however, been found that increased contents of nitroaromatics can occur in the reactors according to the prior art, especially in the stream below the internal loop at the transition to the external loop, i.e. in the vicinity of the reactor outlet.

The abovementioned reactors and corresponding processes according to the prior art have, in particular, the disadvantage that, when they are designed for large circulated volumes, they cause short circuit streams which, undesirably, lead to the stream from the reactor going into the external circulatory flow without having gone through a distance necessary for the reaction in the reactor. As a result, the concentration of the liquid reactant does not decrease sufficiently before it leaves the reactor.

In the case of strongly exothermic reactions and desired high space-time yields, a large number of heat exchanger tubes is necessary for removing the heat of reaction and, for reasons of the specific surface area in a limited reactor volume, these have to be arranged very close together. As a result, the stream flows past the heat exchanger tubes and the heat uptake by the cooling medium is greatly restricted.

It was the object of the present invention to avoid the abovementioned disadvantages. In particular, an apparatus for carrying out gas-liquid reactions which is suitable for particularly large quantities of heat and for high space-time yields should be found.

This object is achieved by an apparatus for the continuous reaction of liquids with gases, in particular for the preparation of toluenediamine by hydrogenation of dinitrotoluene, which comprises a vertically elongated reactor in which there is a reaction space,
at least one heat exchanger comprising heat exchanger tubes which are arranged within the reactor,
at least one inlet for introducing the cooling medium into the heat exchanger,
at least one outlet for taking the cooling medium off from the heat exchanger,
at least one inlet for introducing the gaseous reactant into the reaction space,
at least one inlet for introducing the liquid reactant into the reaction space,
at least one mixing chamber,
at least one downward-directed driving jet nozzle for introducing the reaction medium, the outlet of which is arranged above the at least one mixing chamber and which is in fluid connection with the reaction space,
at least one outlet for taking the reaction medium off from the reactor and
at least one means arranged below the heat exchanger and below the mixing chamber for diverting the reaction medium flowing downward through the mixing chamber in such a way that the reaction medium once again flows upward through the heat exchanger, wherein the region surrounding the heat exchanger tubes is in fluid connection with the inlet for introducing the cooling medium and the outlet for taking off the cooling medium and the inner region of the heat exchanger tubes forms part of the reaction space and is in fluid connection with the at least one driving jet nozzle and the outlet for taking off the reaction medium.

This object is additionally achieved by a process for the continuous reaction of liquid reactants with gaseous reactants in the abovementioned apparatus.

The reactor of the apparatus of the invention comprises a bounded space (defined by a vessel) and is designed to allow particular reactions to proceed under defined conditions and to be able to control these reactions. The term "reactor" comprises all regions within the bounded space, i.e. the reaction space, the gas space and the space taken up by the cooling medium (cooling region).

For the purposes of the present invention, a vertically elongated reactor is a reactor which has a larger dimension in the vertical direction (longitudinal direction of the reactor) than in the horizontal direction (transverse direction of the reactor). During operation, the reactor is vertically upright. For the purposes of the present invention, "during operation" means while the process of the invention is being carried out.

For the purposes of the present invention, the terms top, bottom, beside, above and below relate to the vertical direction (longitudinal direction) of the reactor, i.e. they relate to an elongated arrangement.

The reaction space of the reactor is the space within the reactor which is provided for accommodating the reaction medium and accordingly comprises all regions within the reactor which are in fluid connection with the reaction medium during operation.

Fluid connection means the physical connection within the reactor between any two places or elements via which a fluid, i.e., in particular, the reaction medium or the cooling medium, can get from one place or from one element to the other place or to the other element.

A reaction space denotes, in particular, a region within the reactor in which the reaction proceeds during operation and in which means of cooling are provided. As a result, the reaction can proceed essentially without significant temperature changes, i.e. essentially isothermally, in the reaction space.

A heat exchanger is a means of transferring heat to a cooling medium for the purpose of removing the heat of reaction liberated.

According to the invention, the heat exchanger comprises heat exchanger tubes. The heat exchanger is located within the reactor and determines the heat-exchange area between the reaction space and the cooling region. The inner region of the heat exchanger tubes is part of the reaction space.

Heat exchanger tubes are in this case hollow bodies which are provided at the ends with openings and are, in particular, elongated, i.e. have a length greater than an internal diameter. In particular, the ratio of length to internal diameter is at least 10, preferably at least 20, particularly preferably at least 50, in particular at least 100. The heat exchanger tubes also separate the reaction medium from the cooling medium and allow transfer of heat between the two media. The cross section of the tubes is preferably essentially circular. However, it is possible in principle to deviate from the circular shape in order to achieve particular flow configurations.

The diameter of an individual heat exchanger tube is preferably from 10 to 100 mm, in particular from 20 to 50 mm. The heat exchanger tubes are preferably installed vertically in the reactor, i.e. in the longitudinal direction of the reactor.

The heat exchanger tubes are preferably arranged as a bundle of tubes. For the purposes of the present invention, a bundle of tubes is at least two parallel heat exchanger tubes. Bundles of tubes are particularly suitable for taking up large quantities of heat. A person skilled in the art will select the number of tubes in the bundle of tubes corresponding to the necessary heat transfer area based on the volume of the reaction space. The number of heat exchanger tubes in the reactor is preferably at least 100, in particular at least 200, more preferably at least 300, very particularly preferably at least 500. Furthermore, the number of heat exchanger tubes in the reactor is preferably at most 10 000, in particular at most 7000, particularly preferably at most 5000, very particularly preferably at most 4000.

The bundle of tubes is preferably installed within the vertically elongated reactor and around the at least one mixing chamber and, if present, around the diffuser (i.e. the bundle of tubes completely surrounds the mixing chamber and if applicable the diffuser in the vertical direction) and preferably takes up at least 20% by area, in particular at least 30% by area, particularly preferably at least 40% by area, very particularly preferably at least 50% by area, of the internal horizontal cross section of the reactor.

The number of tubes in the bundle of tubes is preferably from 100 to 10 000, particularly preferably from 500 to 5000. A person skilled in the art will select the number, length and diameter of the heat exchanger tubes as a function of, in particular, the heat of reaction liberated per unit time and per unit volume, which determines the temperature difference and heat transfer area required for the removal of heat.

The ratio of the number of heat exchanger tubes to the number of ejectors in the reactor is preferably at least 100, in particular at least 200, particularly preferably at least 500. The abovementioned ratio of heat exchanger tubes to ejectors is preferably at most 10 000, in particular at most 7500, particularly preferably at most 5000.

The abovementioned measures in respect of the number of heat exchanger tubes in the reactor ensures that the internal circulation flow is in fluid connection with a plurality of heat exchanger tubes. In the region of the abovementioned ratios, an advantageous internal circulation flow is achieved in operation and at the same time a large quantity of heat is transferred.

According to the invention, the reactor is designed so that, during operation, the cooling medium surrounds the heat exchanger tubes and the reaction medium flows through the interior of the heat exchanger tubes. The term reaction medium refers to the mixture of the starting materials and products in the reactor, i.e. the starting materials, the reacting mixture and/or the reaction product. The reaction medium is, in particular, a multiphase mixture composed of reaction liquid, dispersed gas and possibly suspended solid catalyst.

This is achieved according to the invention by the region surrounding the heat exchanger tubes being in fluid connection with the inlet for introducing the cooling medium and the outlet for taking off the cooling medium, so that the heat exchanger tubes are surrounded by the cooling medium during operation of the reactor. At the same time, the inner region of the heat exchanger tubes is part of the reaction space and is in fluid connection with the at least one driving jet nozzle and the at least one outlet for taking off the reaction medium, so that the reaction medium flows through the interior of the heat exchanger tubes during operation of the reactor.

The heat exchanger tubes are, in particular, in fluid connection with the at least one driving jet nozzle and the outlet for taking off the reaction medium from the reactor in such a way that, during operation, the reaction mixture firstly flows through the driving jet nozzle, then the mixing chamber and the diffuser, subsequently the heat exchanger tubes and finally the outlet for taking off the reaction medium from the reactor.

In this way, local temperature increases in the case of large quantities of heat liberated are avoided and the space utilization of the reactor volume or the heat removal and the residence time distribution in the reactor are optimized. In particular, a large number of heat exchanger tubes located in close physical proximity can be realized in this way without (for example, in the case of the use of field tubes) constricted flow paths between the tubes, which otherwise lead to local temperature increases due to spatially inhomogeneous heat transfer, occurring.

The heat transfer area based on the reaction volume is preferably from 20 to 400 $m^2/m^3$, in particular from 25 to 300 $m^2/m^3$, particularly preferably from 40 to 100 $m^2/m^3$.

In addition, the apparatus of the invention has at least one gas space in the upper region of the reactor during operation. The gas space in the upper region of the reactor is the space within the reactor which is located above the surface of the liquid of the reaction medium. Accordingly, the gas space is filled with the gaseous reactants and possibly inert gas during operation.

The apparatus of the invention additionally comprises at least one inlet for introducing the cooling medium into the heat exchanger.

For the purposes of the present invention, an inlet is any means provided for allowing the appropriate medium to enter. Correspondingly, an outlet is, for the purposes of the present invention, any means provided for allowing the appropriate medium to leave. The abovementioned means can be, in particular, openings, tubes, valves or nozzles.

The apparatus of the invention additionally comprises at least one outlet for taking the cooling medium off from the heat exchanger. The inlet for introducing the cooling medium into the heat exchanger is preferably installed in the lower region of the reactor, in the vertical direction above the lower end of the reaction space and below the outlet for taking off the cooling medium. In this case, the cooling medium flows into the heat exchanger from the bottom upward.

The outlet is preferably installed in the vertical direction at the level below the upper end of the reaction space.

The apparatus of the invention additionally comprises at least one inlet for introducing the gaseous reactant into the reactor. The inlet for introducing the gaseous reactant is preferably located in the vertical direction at the level below the heat exchanger but above the means of diverting the reaction medium which flows downward through the mixing chamber. Since the abovementioned diversion occurs in such a way that the reaction medium flows upward through the heat exchanger again, an internal circulatory flow is established during operation of the apparatus, so that it is also possible to speak of diversion of an internal circulatory flow.

Installation below the heat exchanger makes it possible to minimize the energy consumption for introduction of the gaseous reactant since the internal circulatory flow can be optimally utilized for mixing and can additionally be reinforced by the buoyancy.

To achieve rapid and uniform mixing of the reaction medium during operation, it is advantageous to distribute the gaseous reactant over part, preferably at least 50%, in particular at least 70%, particularly preferably at least 80%, of the cross-sectional area of a horizontal cross section through the reaction space below the heat exchanger tubes. In principle, any means which has a sufficiently large number of suitably arranged outlet openings is suitable for this purpose. In addition, the cross section of the outlet opening is of importance. In this respect, outlet openings having a diameter of from 1 to 20 mm, in particular from 3 to 10 mm, are advantageous. In this respect, a velocity in the outlet openings of from 5 to 300 m/s, in particular from 10 to 200 m/s, is also advantageous.

Due to the use of a bundle of tubes as heat exchanger, an embodiment specifically matched to the heat exchanger is preferred, since the reaction medium is present in the interior region of the tubes during operation.

In an alternative embodiment, the gaseous reactant is introduced from above, i.e. the inlet for introducing the gaseous reactant is located above the heat exchanger, preferably in the gas space. A disadvantage here is that more energy has to be employed in order to introduce the gaseous reactant. However, an advantage is that the uniform distribution of the gaseous reactant in the reaction space can be achieved particularly simply. However, the above-described introduction below the lower end of the heat exchanger tubes and above the middle of the means for diverting the internal circulatory flow is preferred.

In a particularly preferred alternative embodiment, a further inlet for introducing the gaseous reactant is provided below the lower end of the heat exchanger tubes and above the means for diverting the internal circulatory flow in addition to the abovementioned embodiment of introduction above the heat exchanger. In this way, uniform distribution of the gaseous reactant can be achieved with a low energy consumption for introduction.

The apparatus of the invention additionally comprises at least one inlet for introducing the liquid reactant into the reactor. The at least one inlet for introducing the liquid reactant is preferably at least one tube installed above the mixing chamber, in particular in the gas space. In an alternative embodiment, a liquid nozzle can be used. The inlet for the liquid reactant is preferably installed in the immediate physical proximity of the driving jet nozzle. In this way, more rapid and more complete mixing of the liquid reactant with the reaction medium is possible.

The feed line for the liquid reactants can be cooled up to the inlet, preferably within the reactor, in order to prevent thermally sensitive reactants from being heated too strongly. This is particularly advantageous in the hydrogenation of dinitrotulene. In this case, the reactant is maintained at temperatures of from 60 to 150° C., preferably from 70 to 110° C. The feed line for the dinitrotoluene is particularly preferably surrounded by two concentric jacket tubes: the cooling medium flows through the inner jacket tube to the tip of the feed line and back out again in the outer jacket tube. The liquid reactant is preferably introduced in such a way that it is not in close physical proximity to the reaction medium during operation.

The apparatus of the invention additionally comprises at least one downward-directed driving jet nozzle which is arranged vertically in the gas space of the reactor. The downward-directed installation makes it possible for the gaseous reactant to be drawn into the gas space automatically, i.e. by means of the driving jet nozzle. The driving jet nozzle is operated by means of liquid (the reaction medium) and is thus a liquid nozzle.

The driving jet nozzle or driving jet nozzles can in each case be configured as a one-orifice nozzle or multiorifice nozzle. A one-orifice nozzle has a nozzle underside having precisely one opening, known as the mouth. Correspondingly, a multiorifice nozzle has a nozzle underside having a plurality of openings.

A one-orifice nozzle is simple to produce. A multiorifice nozzle makes particularly effective drawing-in of the gaseous reactants possible, so that the surface of the liquid can be kept at a minimal distance from the driving jet nozzle. If the various mouths of a multiorifice nozzle are arranged on different horizontal levels, the surface of the liquid can be kept particularly stably at a minimal distance from the driving jet nozzle.

Multiorifice nozzles having a round cross section of the openings and a diameter of the openings of from 5 to 100 mm, preferably from 10 to 80 mm, particularly preferably from 20 to 50 mm, are particularly advantageous.

In a particularly preferred embodiment, the one-orifice nozzle or the multiorifice nozzle comprises openings which are not rotationally symmetric, in particular star-shaped or annular cross sections. Cross-shaped or slotted openings can also be advantageous. In the case of such non-circular embodiments, it is important that the hydraulic diameter be reduced compared to a rotationally symmetric opening. For the purposes of the present invention, the hydraulic diameter is four times the cross-sectional area of the opening divided by the circumference of the opening. It is advantageous to use hydraulic diameters of from 5 to 100 mm, preferably from 10 to 80 mm, particularly preferably from 20 to 50 mm, per opening.

Configuration of the driving jet nozzle or driving jet nozzles as multiorifice nozzle is particularly preferred.

Each driving jet nozzle is arranged in the vertical direction above a mixing chamber. In a preferred embodiment, each driving jet nozzle is assigned its own mixing chamber, with particular preference being given to using multiorifice nozzles.

During operation of the present invention, momentum exchange takes place in the mixing chamber.

The driving jet nozzle is preferably installed so that, during operation, the lower end of the nozzle is at a distance of from 0 to 10 times the diameter of the driving jet nozzle, preferably from 0.5 to 2 times the diameter of the driving jet nozzle, from the surface of the reaction medium. This achieves an optimal drawing-in action in respect of the gaseous reactants.

In an alternative embodiment, a particular proportion of the length of the driving jet nozzle dips through the gas-liquid interface into the liquid. The introduction of gas then occurs only via the fresh gas feed line below the heat exchanger.

To improve mixing between the reactants and the reaction medium further, at least one inlet for the liquid reactant can be provided per driving jet nozzle.

The apparatus of the invention additionally comprises at least one outlet for taking the reaction medium off from the reactor. The outlet for taking the reaction medium off from the reactor is preferably installed at the lower end of the reactor. In a preferred embodiment, the outlet is located below the means for diverting the internal circulatory flow. Accordingly, the outlet is preferably located outside the internal circulatory flow during operation. The reaction medium is taken off from the internal circulatory flow by a further means which is different from the outlet for taking the reaction medium off from the reactor.

The outlet for taking the reaction medium off from the reactor and the at least one driving jet nozzle for introducing the reaction medium are in fluid connection with one another via an external circuit during operation of the apparatus of the invention.

The way in which the reaction medium is taken off from the internal circulatory flow before the reaction medium is taken off from the reactor is important here. The taking-off of the reaction medium from the internal circulatory flow is preferably carried out directly before the inlet for the liquid reactant. As a result, the reaction product is taken off from the internal circulatory flow at a place at which maximum conversion based on the liquid reactant is present.

The reaction medium is thus preferably taken off from the internal circulatory flow in close physical proximity to the inlet for introduction of the liquid reactant.

Preference is thus given to the reaction medium after it has been taken off from the internal circulatory flow flowing downward in a layer along the outer wall of the reactor before being taken off from the reactor. The reaction medium here particularly preferably flows downward through the interior of heat exchanger tubes arranged in the outer region of the reaction space and is thus cooled further along this path.

In an alternative embodiment, the outlet for taking the reaction medium off from the reactor is located in the upper region of the reactor. In this embodiment, the outlet for taking the reaction medium off from the reactor is located in close physical proximity to the place in which the reaction medium is taken off from the internal circulatory flow.

In a further alternative embodiment, the reaction medium is taken off from the internal circulatory flow in the lower region of the reactor and subsequently flows downward past the means for diverting the internal circulatory flow and is then taken off from the reactor and fed to the external circulatory flow (i.e. is drawn in by the stream through the pumps). However, this embodiment is less preferred.

During operation of the apparatus of the invention, at least one pump is arranged in an external circuit which forms the fluid connection between the outlet for taking the reaction medium off from the reactor and the at least one driving jet nozzle, so that the reaction medium is correspondingly pumped from the outlet for taking the reaction medium off from the reactor to the driving jet nozzle. The apparatus of the invention therefore preferably comprises at least one pump which is arranged in an external circuit and fluidically connects the outlet for taking the reaction medium off from the reactor to the at least one driving jet nozzle. The energy input for the external circulatory flow is thus effected by means of at least one pump, for which reason a pumped stream can be spoken of here. The internal circulatory flow is driven by the driving jet nozzle, for which reason a drawing-in stream can be spoken of here.

Each mixing chamber together with the driving jet nozzle or driving jet nozzles arranged above forms a jet pump, which is referred to as ejector. In a preferred embodiment, the ejector additionally comprises a diffuser which is connected to the lower end of the mixing chamber. This means in particular that diffuser and mixing chamber are physically connected to one another, i.e. adjoin one another directly and thus form a unit. The diffuser is thus distinct from the mixing chamber in the context of the present invention.

A diffuser is formed by a widening, preferably a funnel-shaped widening, of the cross section compared to the mixing chamber. The mixing chamber is preferably formed by a cylindrical plug-in tube.

When a diffuser is used, an improvement in mass transfer at the phase interface occurs as a result of the kinetic energy of a liquid jet having a high velocity being utilized for drawing-in and dispersing the gas phase. Due to the high energy input, high turbulence and high shear forces are generated in the ejector with the consequence that the gas is dispersed in the form of very small bubbles, i.e. that a very high volume-specific gas-liquid interface is generated. The overall function of the diffuser is to increase the efficiency of the internal circulatory flow.

The mixing chamber is, in a preferred embodiment, formed by a plug-in tube.

The mixing chamber or mixing chambers is/are preferably each connected at its/their lower end to a diffuser. In a vertical direction below the diffuser, there is, in a preferred embodiment, a cylindrical extension of the diffuser in the form of a tube having a constant diameter.

In a particularly preferred embodiment, an ejector which is arranged from the top downward in the driving jet direction and is formed by one or more driving jet nozzles, a mixing chamber, optionally a diffuser and optionally further cylindrical sections comprises at least three sections underneath the driving jet nozzles: an upper section which has an essentially round cross section having the diameter d1, a diffuser as middle section whose cross section widens compared to the upper section from the top downward and a lower section which has an essentially round cross section having the diameter d2, where d2>d1.

In a preferred embodiment, the plug-in tube as mixing chamber has a rounded intake at the upper end, i.e. the plug-in tube has a slight widening of the internal diameter in the region of the upper end. This leads to an improved drawing-in action in respect of the reaction medium with avoidance of flow losses.

In a preferred embodiment, a plurality of ejectors are used. This accelerates mixing-in of the feedstreams. In addition, this embodiment is particularly efficient in combination with the crossflow filtration described below since this leads to predivision of streams. The individual tubes of this predivision can thus advantageously each be connected to a driving jet nozzle.

Basically, the mixing distance required for sufficient mixing is generally from five to ten times the diameter of the mixing chamber. In the case of a plurality of ejectors, the efficiency of mixing is thus increased overall, i.e. satisfactory mixing is established more quickly in the flow. The direct gas input through the driving jet nozzle is also improved in this way because the contact area between gas and liquid is increased.

In a further embodiment, the driving jet nozzle which is arranged in the upper region of the reactor is configured as an annular gap nozzle and the gaseous reactant, preferably hydrogen, is fed into the reactor via an annular gap at the outer wall of the driving jet nozzle configured as two-jet nozzle.

To establish an internal circulatory flow during operation of the reactor, means which divert the flow below the heat exchanger sidewards are provided, as a result of which an internal circulatory flow is obtained in the reactor.

Accordingly, the apparatus of the invention comprises at least one means for diverting the internal circulatory flow, with the at least one means being installed within the reactor and underneath the heat exchanger. The means for diverting the flow of the reaction medium is preferably a diversion pan.

A diversion pan has a surface oriented in the transverse direction of the reactor and a lateral border extending in the longitudinal direction of the reactor and pointing upward, i.e. in the direction of the ejector. In an alternative embodiment, the means for diverting the flow of the reaction medium is an impingement plate. An impingement plate has a surface oriented in the transverse direction of the reactor and no lateral border extending in the longitudinal direction of the reactor. A diversion pan is preferred. This makes it possible to avoid short circuit flows in the lower region of the reactor and particularly effectively set very low product concentrations at the outlet for taking the reaction medium off from the reactor.

The diversion pan preferably extends in the horizontal plane in the transverse direction of the reactor over a majority of the heat exchanger tubes but preferably not over the entire cross section of the heat exchanger tubes. As a result, the reaction medium in the outer region of the reactor can get to the outlet for taking the reaction medium off from the reactor only after it has flowed upward into the tubes above the diversion pan. The reaction medium preferably flows upward in the tubes above the diversion pan and a substream then flows downward again in the tubes outside the cross section of the diversion pan.

The horizontal cross-sectional area of the diversion pan is preferably from 60 to 98% of the area taken up by the lower end of the heat exchanger in the cross section of the reactor, in particular from 70 to 95%, particularly preferably from 75 to 90%.

The height of the border of the diversion pan is from 1 to 30% of the longest diameter of the diversion pan, in particular from 2 to 20%, particularly preferably from 3 to 15%. The angle of the border relative to the inner surface of the diversion pan is preferably from 90 to 170°, in particular from 90 to 150°, particularly preferably from 90 to 120°.

In a preferred embodiment, the diversion pan has emptying openings which can, in particular, be at least partly closed. During operation, the openings are at least partly or preferably completely closed, whereas they can be opened when the apparatus is not operating.

In an alternative embodiment, the bottom of the reactor is the means for diverting the reaction medium flowing downward through the mixing chamber. In this case, the outlet for taking the reaction medium off from the reactor is installed above the underside of the heat exchanger of the reactor.

According to the invention, the region surrounding the heat exchanger tubes is connected to the inlet for introduction of the cooling medium and the outlet for taking off the cooling medium in such a way that the heat exchanger tubes are surrounded by the cooling medium during operation of the reactor.

According to the invention, the inner region of the heat exchanger tubes is additionally connected to the driving jet nozzles and the outlet for taking off the reaction medium in such a way that the reaction medium flows through the interior of the heat exchanger tubes during operation of the reactor.

In an embodiment of the invention, a heat exchanger is provided in the external circuit, which can also be referred to as external loop flow. Any remaining part of the heat of reaction can thus be removed via a heat exchanger arranged in the external circuit. A shell-and-tube heat exchanger is preferably used here.

The gas space can also be referred to as gas disengagement space. In a preferred embodiment, means for gas disengagement, preferably metal plates which in the horizontal plane do not extend to the periphery of the reactor, so that the reaction mixture can flow undisturbed in the outer region to the outlet from the reactor, are located above the heat exchanger and below the surface of the liquid. In the middle, the means for gas disengagement have at least one opening so that gas can ascend in the region of the driving jet nozzles. The gas which rises in the reaction space collects at the metal plates and is partly sucked downward again by the internal circulatory flow (drawing-in stream).

The volume of the gas in the reaction medium should be set as a function of the materials properties to from 5 to 20% by volume, based on the volume of the reaction medium, during operation.

If the level of the surface of the liquid in the reactor is kept constant (e.g. by use of a multiorifice nozzle), the gas content is preferably regulated by adaptation of the amount of reaction product discharged. As an alternative, the level of the surface of the liquid in the reactor can also be regulated by adaptation of the amount of reaction product discharged and the gas content can then be influenced, for example, via the amount of fresh gas introduced underneath the heat exchanger.

The reactor can in principle be made of any material which has the necessary mechanical and thermal stability and compatibility with the product. The reactor is preferably made of steel (e.g. 1.0037 or 1.0565), particularly preferably of stainless steel (e.g. 1.4541 or 1.4571) and/or of duplex steel (e.g. 1.4462). It goes without saying that combinations of stainless steel and/or duplex are also possible for, for example, parts which are in contact with product and parts which are not in contact with product can be made of an alloyed steel.

Processes

The apparatus of the invention is preferably used for the reaction of gases with liquids. The reaction is preferably a hydrogenation, oxidation or acetylation, particularly preferably a hydrogenation. Here, preference is given to hydrogenating nitroaromatic compounds.

In the process of the invention, preference is given to using aromatic nitro compounds having one or more nitro groups and from 6 to 18 carbon atoms, for example nitrobenzenes such as nitrobenzene, 1,3-dinitrobenzene, nitrotoluenes such as 2,4-, 2,6-dinitrotoluene, 2,4,6-trinitrotoluene, nitroxylenes, such as 1,2-dimethyl-3-, 1,2 dimethyl-4-, 1,4-dimethyl-2-, 1,3-dimethyl-2-, 2,4-dimethyl-1- and 1,3-dimethyl-5-nitrobenzene, nitronaphthalenes such as 1-, 2-nitronaphthalene, 1,5 and 1,8-dinitronaphthalene, chloronitrobenzenes such as 2-chloro-1,3-, 1-chloro-2,4-dinitrobenzene, o-, m-, p-chloronitrobenzene, 1,2-dichloro-4-, 1,4-dichloro-2-, 2,4-dichloro-1- and 1,2-dichloro-3-nitrobenzene, chloronitrotoluenes such as 4-chloro-2,4-chloro-3-, 2-chloro-4- and 2-chloro-6-nitrotoluene, nitroanilines such as o-, m-, p-nitroaniline; nitro alcohols such as tris(hydroxymethyl)nitromethane, 2-nitro-2-methyl-, 2-nitro-2-ethyl-1,3-propanediol, 2-nitro-1-butanol and 2-nitro-2-methyl-1-propanol and also any mixtures of two or more of the nitro compounds mentioned.

Preference is given to hydrogenating aromatic nitro compounds, preferably mononitrobenzene, mononitrotoluene or dinitrotoluene and in particular 2,4-dinitrotoluene or industrial mixtures thereof with 2,6-dinitrotoluene, where these mixtures preferably have up to 35% by weight, based on the total mixture, of 2,6-dinitrotoluene and proportions of from 1 to 4% of vicinal DNT and from 0.5 to 1.5% of 2,5- and 3,5-dinitrotoluene, to the corresponding amines by the process of the invention. Particular preference is given to using the industrial DNT mixture in the isomer composition in which it is obtained in the two-stage nitration of toluene.

In particular, the process of the invention can be advantageously used in the hydrogenation of dinitrotoluene isomers to the corresponding toluenediamine derivatives (TDA), in the hydrogenation of o- or p-mononitrotoluene to o- or p-toluidine and in the hydrogenation of mononitrobenzene to aniline.

The preferred embodiment of the hydrogenation of dinitrotoluene is described in more detail below.

Dinitrotoluene is preferably fed in at the upper end of the reactor, preferably in the gas space above the surface of the liquid in the reactor. The dinitrotoluene is, for the purpose of uniform introduction, advantageously introduced directly into the mixing chamber, particularly preferably into the vortex generated by the jet from the driving jet nozzle. Preference is given to using a mononitro and/or polynitro compound in pure form, as mixture with the corresponding monoamine and/or polyamine, as a mixture with the corresponding monoamine and/or polyamine and water or as a mixture with the corresponding monoamine and/or polyamine, water and a solvent, in particular an alcoholic solvent. The aromatic mononitro and/or polynitro compound is introduced finely dispersed into the mixture.

In a preferred embodiment of the process of the invention, the introduction of the nitroaromatic is effected through a feed line and a metering device without the geometric possibility of dead space formation. Corresponding units or apparatuses are known per se to those skilled in the art. It is advantageous for direct physical contact between the introduction for the nitroaromatic and the liquid phase, preferably comprising the aromatic amine, i.e. the corresponding reaction product, water and catalyst, not being able to occur in the reactor and/or in the pumped circuit when the full height of the reactor is correct either in the operating state or after shutdown. This is achieved, in particular, by the distance between the inlet for the nitroaromatic and the liquid phase being, for example, from 0.01 to 3 m, preferably from 0.05 to 1.0 m.

In a further preferred embodiment of the process of the invention, the introduction of the nitroaromatic is effected via one or more independent pipes for which partial or complete blocking can be detected by instrumentation.

Pipes of this type are known per se to those skilled in the art. The pipes which are preferably used are, for example, made of metal, for example black steel or stainless steel. The pipes preferably have a diameter which is dimensioned according to the amount of nitroaromatics which are fed in.

In general, the pipes which are preferably used can have any suitable cross section. Preference is given to using pipes having a DN50 or less, particularly preferably DN40 or DN25, since these act as a detonation barrier.

In a preferred embodiment, the exit cross section of the inlet for the nitroaromatic at the ends of the one or more independent pipe(s) has a constriction or a shape deviating from the rotationally symmetric shape. The exiting nitroaromatic jet can have laminar or turbulent behavior. A configuration of this type is described, for example, in WO2012/123469.

Introduction of the dinitrotoluene into the gas phase above the surface of the liquid prevents reaction product from flowing back into the feed line for dinitrotoluene and thereby leading to decomposition or explosion of the dinitrotoluene. Pure dinitrotoluene has a decomposition temperature of about 260° C., but the decomposition temperature decreases drastically as soon as toluenediamine and catalyst are mixed in, down to 100° C.

It is therefore also advantageous to flush the feed line for dinitrotoluene with hot water when production is interrupted or the plant is shutdown.

The concentration of nitro groups, i.e. the sum of the products of all nitroaromatics present, in each case multiplied by the number of their nitro groups per molecule, for example in the case of the hydrogenation of dinitrotoluene (DNT) c(nitroaromatics)=c(DNT)·2+c(ANT)·1 (ANT=aminonitrotoluene) or in the case of the hydrogenation of ortho-nitrotoluene (o-NT) c(nitroaromatics)=c(o-NT)

·1, in the liquid phase of the product output from the reactor is preferably set, in the region between the reactor and the downstream product separation unit, to a value in the range from 0 to 2000 ppm by weight, preferably from 0.5 to 1000 ppm by weight, particularly preferably from 1 to 200 ppm by weight and very particularly preferably from 1 to 50 ppm by weight, based on the total weight of the liquid phase of the product output from the reactor. This can both reduce by-product formation and largely avoid catalyst deactivation. Processes of this type are described in WO2011/144481. The abovementioned concentration ranges can be achieved more easily, the faster the mixing-in of the liquid reactants (e.g. by means of a highly efficient driving jet nozzle having a diffuser) and the better short circuit streams are prevented (in particular by means of a diversion pan). Compared to reactors without such aids, these concentrations can therefore be achieved using less catalyst, at a higher space-time yield or a lower temperature (and thus frequently a higher selectivity).

It is advantageous to ensure by means of suitable measures that the concentration of hydrogen in the reaction mixture which flows from the internal circulatory flow into the external loop is not below 1% by volume, preferably 3% by volume, based on the total volume of the reaction mixture which flows into the external loop. For this purpose, it is possible to design the diameter of the reactor or the outflow velocity of the reaction mixture from the reactor or any gas disengagement plates present above the heat exchanger appropriately.

In a further embodiment, it is possible to ensure the minimum concentration of the hydrogen which flows from the internal circulatory flow into the external loop by introducing hydrogen into the reaction mixture which flows from the internal circulatory flow into the external loop, as close as possible to the reactor.

The reaction product is preferably taken off from the external circuit. To be able to drive the external circulation, a pump which can pump not only liquid but also gas and suspended solid has to be installed. Here, up to 20% by volume of gas and 20% by weight of suspended solid should be pumpable. To avoid Ni deposits in the case of Ni-containing catalysts or to avoid excessive breaking down of supported catalysts, an arrangement of a plurality of (preferably two) pumps connected in series or the use of a multistage pump can be useful.

The cooling medium is preferably water. In a preferred embodiment, water is fed in liquid form and taken off as steam. The steam can be utilized for supply of heat or energy within any chemical plant complex. In addition, the steam can also be fed into an existing steam network at the site of the plant.

Steam can be generated both in the internal heat exchanger or any external heat exchanger present from the heat of reaction liberated in two ways: 1) by vaporization of part of the cooling water in the cooling tubes (direct steam generation) or 2) by heating of the cooling water to a pressure which is above the pressure for the steam to be generated and subsequent depressurization to the pressure level of the steam to be generated (flash evaporation). In this depressurization, part of the cooling water vaporizes and the steam/water mixture is cooled to the boiling point corresponding to the pressure of the steam.

Both types of vaporization can be employed both in the internal heat exchanger and in an external heat exchanger. A combination of the two types of vaporization, i.e. direct vaporization in the internal heat exchanger and flash evaporation in an external heat exchanger or vice versa, is likewise possible.

In an alternative embodiment, water from a secondary cooling circuit is at least partly utilized as cooling medium. In a preferred alternative embodiment, one of the two types of steam described is generated in the internal heat exchanger and an external heat exchanger is cooled by means of water from a secondary cooling water circuit.

The reaction in the process of the invention is preferably carried out in the presence of a suspended or dissolved catalyst, particularly preferably in the presence of a suspended catalyst.

Many catalysts have been developed for the hydrogenation of dinitrotoluene to toluenediamine, with improvement of yield and selectivity of the reaction and also the stability of the catalysts even at relatively high reaction temperatures being high priority objectives in the development of new catalysts.

In a first general embodiment of the invention, the process of the invention is, as indicated above, carried out in the presence of a catalyst, in particular in the presence of a supported catalyst which comprises, as active component, nickel alone or together with at least one metal of transition group I, V, VI and/or VIII of the Periodic Table. The preferred catalysts can be produced industrially by application of nickel and optionally at least one of the abovementioned additional metals to a suitable support.

As metals of transition group I, II, V, VI and/or VIII of the Periodic Table, preference is given to using palladium, platinum, rhodium, iron, cobalt, zinc, chromium, vanadium, copper, silver or a mixture of two or more thereof.

Catalysts which comprise an active composition which comprises one or more metals selected from the group consisting of platinum, palladium, rhodium and ruthenium and additionally one or more further metals selected from the group consisting of nickel, cobalt, iron and zinc and has been applied to an inert support have been found to be particularly suitable.

In a preferred embodiment of the invention, the catalyst has a nickel content of from 0.1 to 99% by weight, preferably from 1 to 90% by weight, particularly preferably from 25 to 85% by weight and very particularly preferably from 60 to 80% by weight, based on the total weight of the catalyst.

In a preferred embodiment of the invention, the catalyst comprises Ni and platinum. In a further preferred embodiment of the invention, the catalyst comprises Ni and Al; in a further particularly preferred embodiment, the catalyst comprises nickel, palladium and iron.

Hydrogenation catalysts which comprise platinum and nickel in the form of an alloy having an atomic ratio of nickel to platinum, determined by means of EDXS (energy dispersive X-ray spectroscopy), in the alloy of from 30:70 to 70:30 on a support are particularly advantageous. The atomic ratio of nickel to platinum, determined by means of EDXS (energy dispersive X-ray spectroscopy), is in particular from 45:55 to 55:45.

As support material, preference is given to using activated carbon, carbon black, graphite or oxidic support components such as silicon dioxide, silicon carbide, kieselguhr, aluminum oxide, magnesium oxide, titanium dioxide, zirconium dioxide and/or hafnium dioxide or a mixture of two or more thereof, particularly preferably zirconium dioxide, $ZrO_2$, $HfO_2$ and/or $SiO_2$, $ZrO_2$ and/or $SiO_2$, $ZrO_2$, $HfO_2$.

The supports used are preferably mesoporous and have an average pore diameter of from 35 to 50 nm and a specific surface area of from 50 to 250 $m^2/g$. The surface area of the support is determined by the BET method by means of $N_2$ adsorption, in particular in accordance with DIN 66131. The average pore diameter and the pore size distribution are determined by means of Hg porosimetry, in particular in accordance with DIN 66133.

The application of nickel and optionally the at least one further metal can be achieved by the usual suitable processes as are known to a person skilled in the field of catalyst technology. The supports which have been coated or impregnated with the metal or metal salt by coprecipitation are subsequently dried and calcined by known methods. The coated supports are subsequently activated by treatment in a gas stream comprising free hydrogen. This activation usually takes place at temperatures in the range from 30 to 600° C., preferably in the range from 80 to 150° C. and particularly preferably at 100° C. The gas stream preferably comprises from 50 to 100% by volume of hydrogen and from 0 to 50% by volume of nitrogen. The catalyst produced for the preferred use has a degree of reduction of at least 70% after reduction for one hour at 100° C.

The supported catalysts obtained in this way generally have a nickel metal surface area of from about 10 to about 50 $m^2/g$, preferably from about 20 to about 60 $m^2/g$. The nickel content of the catalysts used in the process of the invention is generally in the range from 0.1 to 99% by weight, preferably in the range from 1 to 90% by weight, particularly preferably in the range from 25 to 85% by weight, based on the total weight of the catalysts used.

Suitable catalysts of this embodiment are described, for example, in the documents EP 1 161 297 A1 and EP 1 165 231 A1.

In a second embodiment of the invention, activated nickel catalysts as described, for example, in WO 2008/145179 A1 are used in the process of the invention. Accordingly, activated nickel catalysts which are based on an Ni/Al alloy and can comprise one or more metals selected from the group consisting of Mg, Ce, Ti, V, Nb, Cr, W, Mn, Re, Fe, Ru, Co, Rh, Ir, Pt, Cu, Ag, Au and Bi are used according to a preferred embodiment of the invention. The degree of doping is in the range from 0.05% by weight to 20% by weight for each doping element. The average particle size of the catalysts used is <25 μm.

In a third embodiment of the invention, catalysts which are described, for example, in WO 2008/138784 A1 are used in the process of the invention. The invention therefore further provides, in a preferred embodiment of the invention, for the use of hydrogenation catalysts comprising a mixture of nickel, palladium and an additional element selected from the group consisting of cobalt, iron, vanadium, manganese, chromium, platinum, iridium, gold, bismuth, molybdenum, selenium, tellurium, tin and antimony as active component on a support for preparing aromatic amines by catalytic hydrogenation of the corresponding nitro compounds, in particular for preparing toluenediamine by hydrogenation of dinitrotoluene. The additional element is preferably selected from the group consisting of cobalt, iron, vanadium, bismuth and tin.

As supports for the catalysts, it is possible to use the materials which are known and customary for this purpose. Preference is given to using activated carbon, carbon black, graphite or metal oxides, preferably hydrothermally stable metal oxides such as $ZrO_2$, $TiO_2$, $Al_2O_3$. In the case of graphite, the HSAGs (high surface area graphites) having a surface area of from 50 to 300 $m^2/g$ are particularly preferred. Particular preference is given to activated carbons, in particular physically or chemically activated carbons, or carbon blacks such as acetylene black.

The preferred catalysts are produced, for example, by placing the support in a reaction vessel and reacting it with an aqueous solution of the palladium and nickel salts together with the additional element. The amount of the water used for dissolving the salts should be such that a kneadable paste is formed. The water is preferably used in an amount of from 100 to 200% by weight of the support composition. As metal salts, use is made of, in particular, nitrates or chlorides, with nitrates being preferred because they are less corrosive. The paste is mixed and the water is then vaporized at low pressure and temperatures in the range from 50 to 100° C., for example in a rotary evaporator or an oven. For safety reasons, vaporization can be carried out in a stream of nitrogen. The fixing of the metals to the support can be effected by reduction by means of hydrogen when using chlorides as metal salts. However, corrosion can occur here. The metals are therefore preferably fixed under alkaline conditions. This is effected, in particular, by addition of an aqueous solution of alkali metal carbonates and subsequent washing of the support until free of anions. As an alternative, the metals can also be precipitated under alkaline conditions, in particular at a pH in the range from 8 to 9, from a supernatant solution onto the support. The support is then dried, preferably as described above, and reduced by means of hydrogen. This can, for example, occur in a rotary bulb furnace. Before the catalyst is taken out, the catalyst is passivated, for example under an inert gas such as nitrogen comprising traces of air, preferably not more than 10% by volume.

The preferred hydrogenation catalysts produced by this process preferably comprise from 0.5 to 5% by weight of palladium, from 10 to 20% by weight of nickel and from 0.5 to 5% by weight of the additional element.

In a further embodiment of the production of the hydrogenation catalysts which are preferably used, the reduction of the catalysts is effected by addition of salts having a reducing action, for example ammonium carboxylates or alkali metal carboxylates, e.g. ammonium formate or sodium formate. For this purpose, the support is suspended in water and the solutions of the metal salts are added simultaneously or after suspension. As metal salts, use is made of, in particular, nitrates or chlorides, with nitrates being preferred because they are less corrosive. The salts having a reducing action are added to this solution and the suspension is heated, for example by boiling under reflux. The catalysts are subsequently washed until free of anions and filtered, for example by means of a filter press or a centrifuge, and used as moist paste. Further examples of the production of the catalysts which are preferably used may be found in WO 2005/037768 A1.

The hydrogenation of dinitrotoluene, of mononitrotoluene and of mononitrobenzene can be carried out in solution. Solvents used are the materials customary for this purpose, in particular lower alcohols, preferably ethanol or methanol. Owing to the optimal flow conditions and the immediate removal of the heat of reaction in the reactor used according to the invention, it is also possible to carry out the hydrogenation without solvent. This has the advantages that the volume of the reaction mixture is smaller, which allows smaller dimensions of the reactor and also of the pumps and pipes, that secondary reactions between the solvent and the starting materials are ruled out and also that the outlay for the work-up of the end products is reduced.

The major part of the reaction mixture is conveyed in the external loop flow; only a small proportion of the reaction mixture is circulated externally by pumping and thus serves to drive the loop flow. The ratio of the volume flows of internal loop flow to external loop flow is from 1:1 to 15:1, preferably from 3:1 to 10:1. Due to the small proportion of the external loop flow based on the total reaction mixture, significantly smaller amounts of catalyst are circulated per unit time through the circulation pump than in the case of cooling exclusively by means of an external heat exchanger. This leads to a reduction in the mechanical stress on the catalyst and thus to a longer life of the catalyst. In addition, this embodiment ensures, in combination with the integrated heat exchangers, a highly isothermic reaction, i.e. a very small temperature gradient over the height of the reactor (typically in the range from 1 to 10 K) since the hydrogenation proceeds virtually entirely in the internal loop flow and the heat of reaction is therefore removed at the place where it arises. Limitations of the reaction rate by mass and heat transfer are virtually completely eliminated here. Secondary reactions, which are promoted by temperature gradients in the reaction system, are virtually completely suppressed. The reaction rate is then limited only by the reaction kinetics. In addition, the safety of the process compared to cooling in an external circuit is improved since the cooling of the reactor still functions when the pump for the external circuit goes down.

The volume flow of the internal loop flow is preferably monitored directly by measuring the pressure difference between the gas space and the cylindrical mixing space. In the case of insufficient loop flow, and thus insufficient mixing in the reactor, the introduction of the liquid starting material is interrupted in order to prevent deactivation of the catalyst.

Dispersing of the individual reactants in combination with the other reaction parameters results in intensive mixing of all components at low substrate concentrations, high mass transfer coefficients and large volume-specific phase interfaces. The arrangement of the cooling tubes parallel to the reactor walls in the reactor leads to the reactor contents being largely free of reaction temperature gradients. Secondary reactions are substantially suppressed and catalyst deactivation is largely avoided by avoidance of local overheating. Thus, high space-time yields are achieved together with high selectivity even at low catalyst concentrations.

Owing to the low concentration of the nitroaromatic in the reaction mixture, catalyst deactivation is largely avoided and thermal decomposition of the nitroaromatic can be reliably prevented.

The hydrogenation of dinitrotoluene is preferably carried out at temperatures of from 80 to 200° C., more preferably from 110 to 190° C., and pressures in the range from 10 to 50 bar, more preferably from 15 to 35 bar.

The catalyst is preferably suspended in the reaction medium. To be able to take off the reaction product without catalyst particles, the reaction product is separated off from the catalyst in the external circuit. The product and catalyst separation unit is generally a filter (e.g. a membrane filter/crossflow filter), a static decanter (e.g. a gravity separator or settler, frequently a lamellar clarifier) or a dynamic decanter (e.g. a centrifuge or a nozzle separator). The catalyst is separated off from the product and subsequently recirculated (in general as a thickened suspension) to the reactor. The discharge of the product is preferably effected with retention of the catalyst. The amine can then be purified by the customary and known methods, for example by distillation or extraction.

The separation of the reaction product from the catalyst is preferably effected by means of membrane filtration.

An advantage of membrane filtration is that it makes rapid and complete retention of the catalysts under mild conditions possible.

The membrane filtration is preferably carried out at a pressure on the suspension side of from 5 to 50 bar, preferably from 20 to 35 bar, a pressure difference between the suspension side and the permeate side of from 0.3 bar to 5 bar and a flow velocity on the suspension side of from 1 to 6 m/s. For the purposes of the present invention, the suspension side is the side of the membrane filter on which the catalyst-comprising mixture is located, while the permeate side is the side of the membrane filter on which the catalyst-free mixture is located.

The membrane filtration can be carried out continuously or batchwise.

In a continuous membrane filtration, at least a substream of the reaction mixture is continually passed through a membrane filter. In this embodiment of the process of the invention, preference is given to arranging the membrane filter in the external circuit of a loop reactor. This embodiment of the process of the invention is preferred.

When the filtration is carried out batchwise, the reaction mixture which has been discharged is passed through a purification stage which can be switched in, comprising a membrane filter and a dedicated circulation pump. In another embodiment of batchwise filtration, the reaction mixture is passed over a membrane filter after the reaction. This embodiment is less preferred since in this case the catalyst separated off has to be concentrated to a greater extent.

The filter membranes used for the process can, for example, be composed of ceramic (e.g. $\alpha$-$Al_2O_3$) or stainless steel (e.g. 1.4404) and preferably have, depending on the particle size of the catalyst used, number average pore diameters in the range from 10 nm to 20 microns, in particular in the range from 50 nm to 10 microns and preferably from 100 nm to 1 micron.

Suitable embodiments of a membrane filtration, in particular crossflow filtration, are known to those skilled in the art and are described, for example, in WO2010/125025, the contents of which are hereby incorporated by reference into the present application.

Despite optimal reaction conditions, moderate deactivation of the catalyst cannot be prevented completely. The external loop therefore preferably has a connection for introduction of fresh catalyst, preferably suspended in water, and a further outlet for discharge of catalyst-comprising reaction product connected to a catalyst discharge unit. This in turn preferably comprises a collection vessel comprising at least one pumping circuit comprising at least one membrane filter.

The invention will be illustrated by examples and drawings. Here, preferred embodiments are described without restricting the invention thereto.

The figures show an apparatus according to the invention, with the regions provided for the reaction medium being denoted by hatching; the regions provided for the cooling medium are not hatched. In FIGS. 1 to 4, specific meanings are:

1—vertically elongated reactor
2—heat exchanger arranged within the reactor,
3—reaction space
4—inlet for introducing the cooling medium into the heat exchanger,
5—outlet for taking off the cooling medium from the heat exchanger,
6—inlet for introducing the gaseous reactant into the reaction space,
7—inlet for introducing the liquid reactant into the reaction space,
8—mixing chamber,
9—downward-directed driving jet nozzle for introducing the reaction medium
10—outlet for taking off the reaction medium from the reactor
11—means (11) arranged beneath the heat exchanger (2) and beneath the mixing chamber (8) for deflecting the reaction medium flowing downward through the mixing chamber (8)
12—diffuser
13—cylindrical section
14—pump 15—external circuit
16—internal circulation flow
17—product isolation unit
18—product
20—heat exchanger tubes
21—the region surrounding the heat exchanger tubes
22—inner region of the heat exchanger tubes

FIG. 3 shows an apparatus according to the invention having four ejectors (transverse section). The region (21) surrounding the heat exchanger tubes is in fluid connection with the inlet (4) for introducing the cooling medium and the outlet (5) for taking off the cooling medium. The inner region of the heat exchanger tubes (22), which forms part of the reaction space, is in fluid connection with the at least one driving jet nozzle (9) and the outlet (10) for taking off the reaction medium from the reactor.

FIG. 4 shows an apparatus which is not according to the invention having four ejectors (transverse section). The inner region of the heat exchanger tubes (22) is in fluid connection with the inlet (4) for introducing the cooling medium and the outlet (5) for taking off the cooling medium. The region (21) surrounding the heat exchanger tubes, which forms part of the reaction space, is in fluid connection with the at least one driving jet nozzle (9) and the outlet (10) for taking off the reaction medium from the reactor. The heat exchanger tubes (22) are typically field tubes in this embodiment.

EXAMPLES

Example 1

According to the Invention

Figure 1:
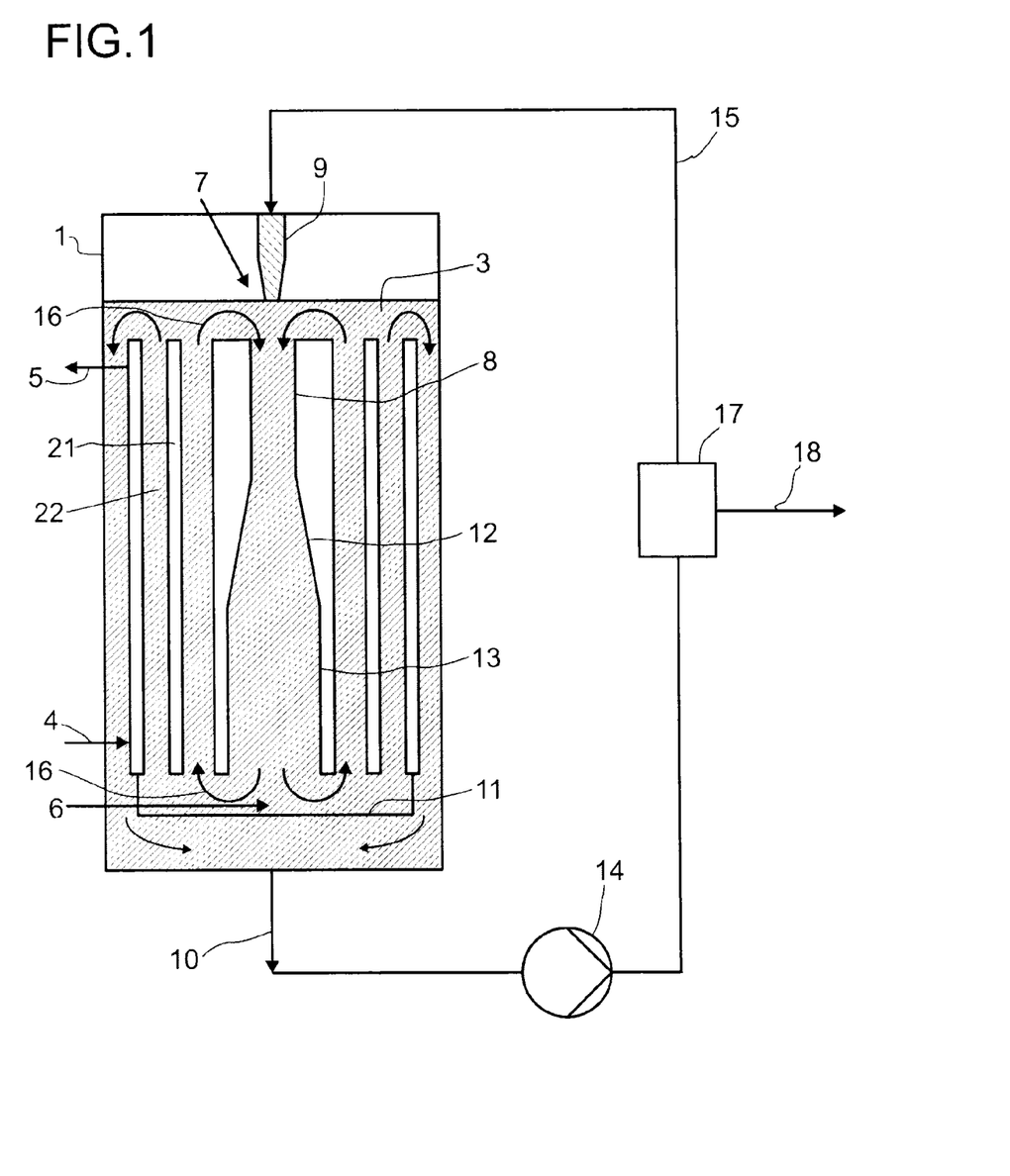
FIG. 1 shows an apparatus according to the invention having one ejector (section in the longitudinal direction).
Figure 3:
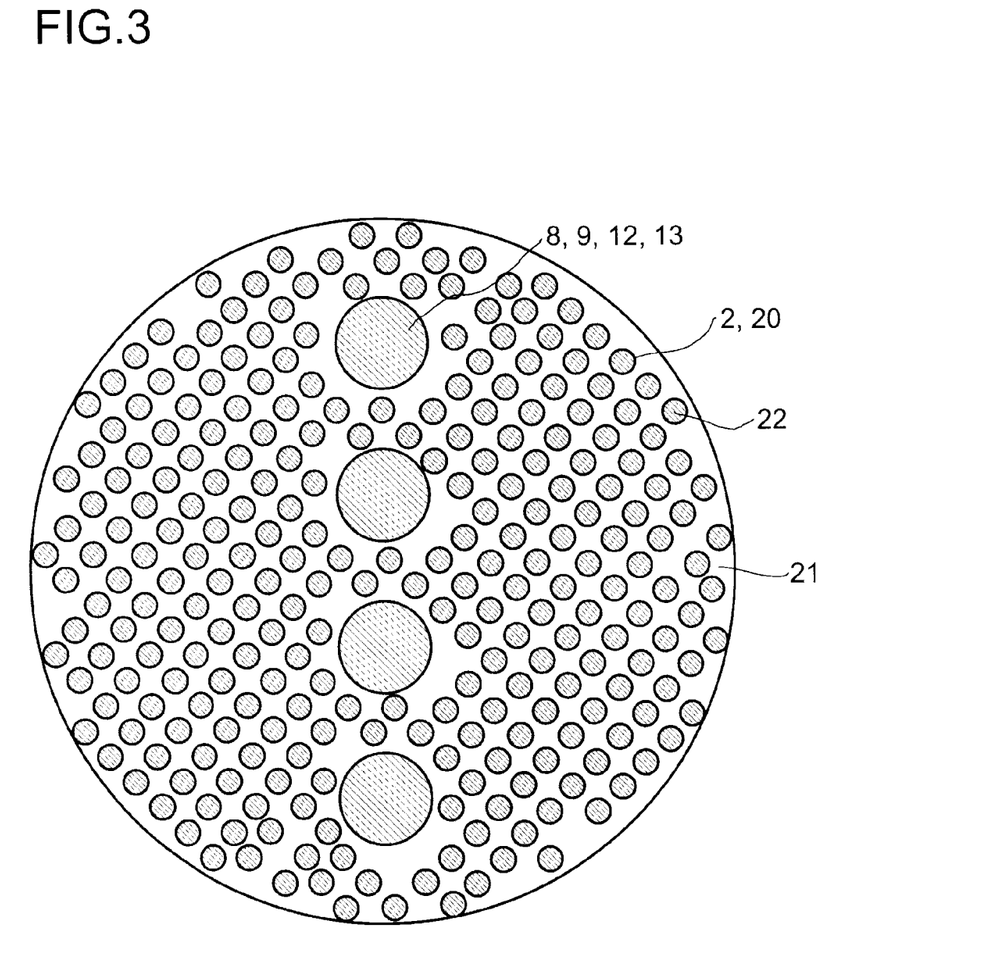

In a reactor as per FIG. 1 and FIG. 3 (one ejector as in FIG. 1) having a fill volume of 10 m$^3$ and a fill height of 10 m up to the means (11) for deflecting the reaction medium flowing downward through the mixing chamber (8), a jet nozzle diameter of 0.08 m, a plug-in tube diameter of 0.32 m, a distance between nozzle mouth and plug-in tube of 0.16 m, a bundle of tubes which surrounds the plug-in tube and through which flow occurs from the bottom upward and which consists of 475 tubes which have a length of 9.5 m and an external diameter of 50 mm and an internal diameter of 46 mm, more than four times the driving jet volume flow of a liquid having a viscosity of 10$^{-6}$ m$^2$/s at a driving jet velocity in the nozzle mouth of 20 m/s could be drawn in and circulated in a simulation.

Example 2

Comparison

Figure 2:
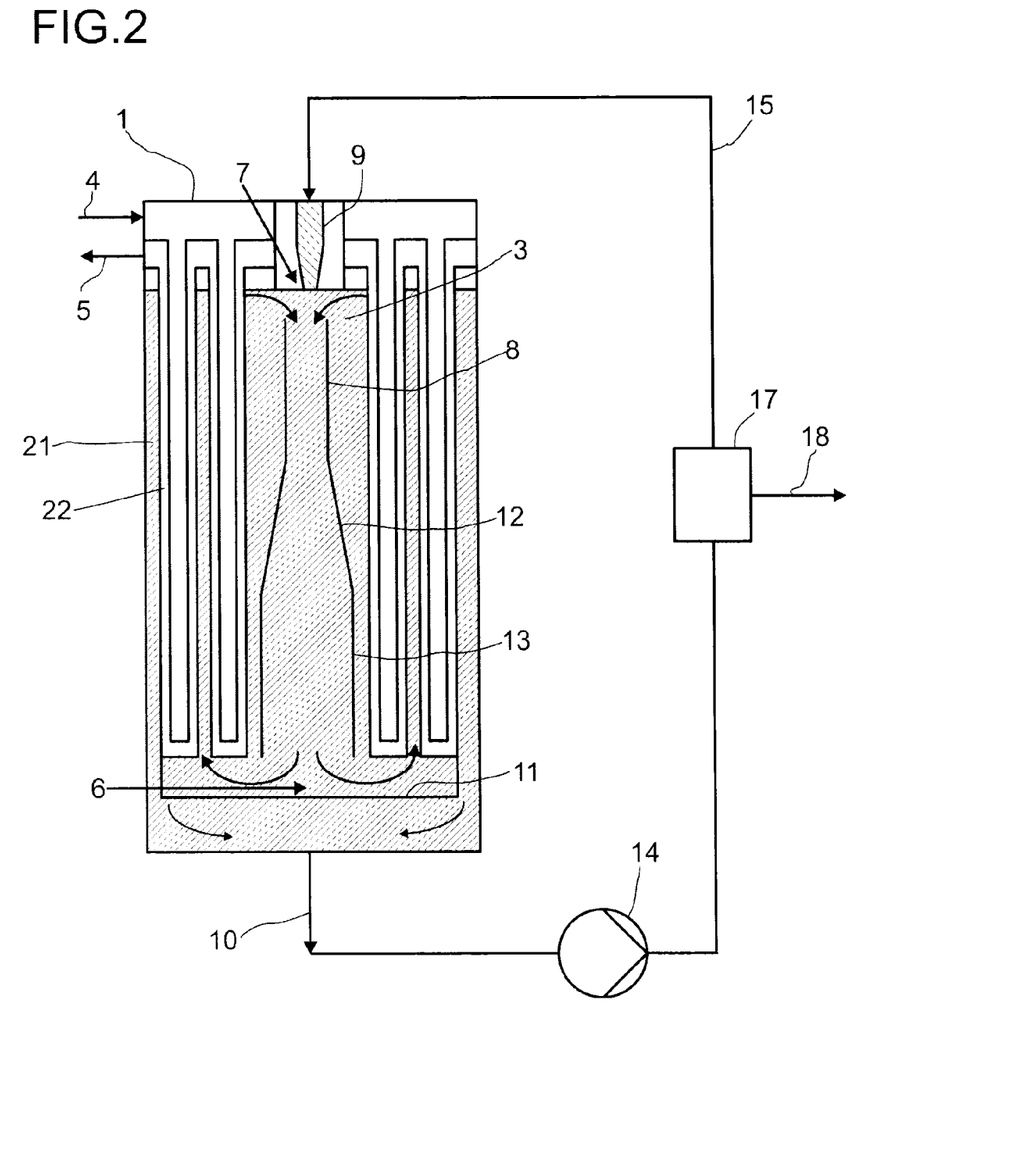
FIG. 2 shows an apparatus which is not according to the invention having one ejector (section in the longitudinal direction), using field tubes as heat exchanger tubes.
Figure 4:
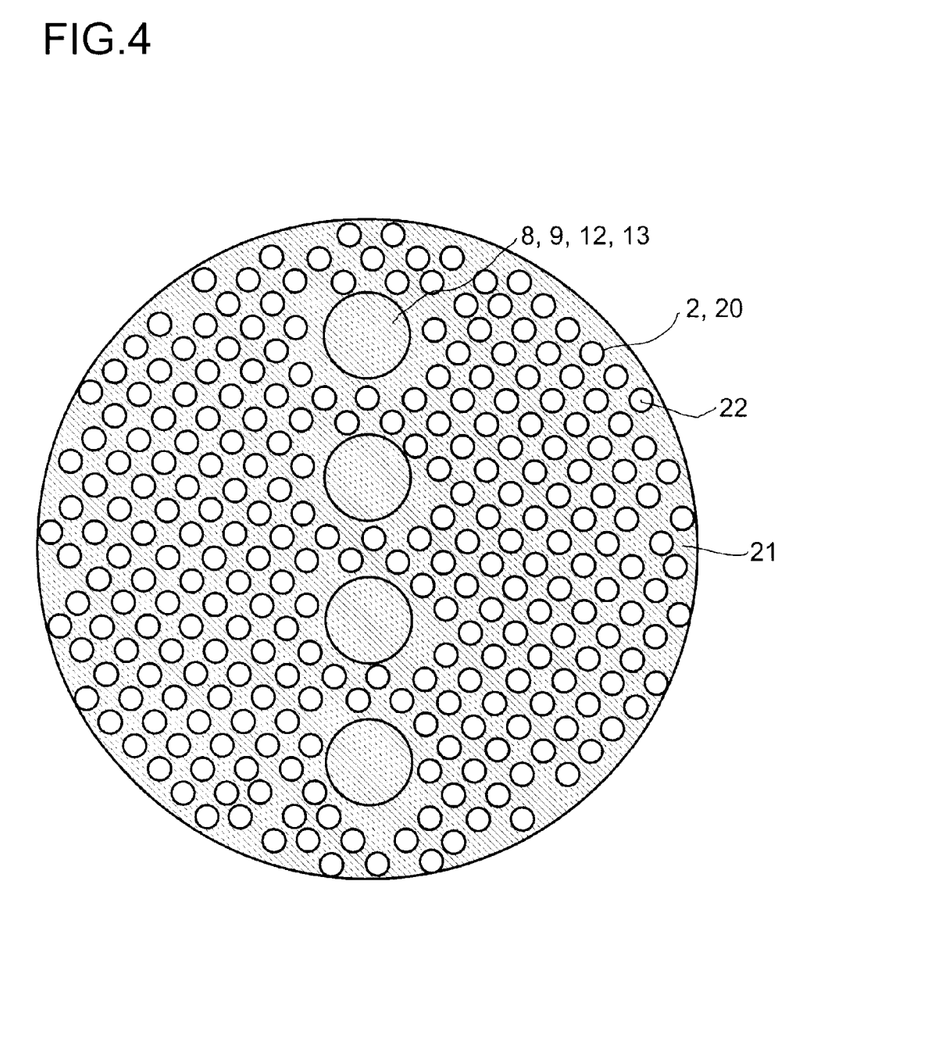

As example 1, but using a reactor as per FIG. 2 and FIG. 4 (one ejector as in FIG. 2). The reaction medium was located in the exterior space of a bundle of tubes consisting of field tubes having an external diameter of 50 mm, the same reaction volume and a tube spacing of 62 mm. In a simulation, the circulated volume flow decreased to less than three times the driving jet volume flow.

Figures

The invention claimed is:

1. An apparatus, comprising:
   a vertically elongated reactor comprising a reaction space,
   a heat exchanger comprising a plurality of heat exchanger tubes arranged within the reactor,
   a first inlet for introducing a cooling medium into the heat exchanger,
   a first outlet for taking the cooling medium off from the heat exchanger,
   a second inlet for introducing a gaseous reactant into the reaction space,
   a third inlet for introducing a liquid reactant into the reaction space,
   a mixing chamber,
   a downward-directed driving jet nozzle for introducing a reaction medium, wherein the driving jet nozzle comprises an outlet arranged above the mixing chamber and in fluid connection with the reaction space,
   a second outlet for taking the reaction medium off from the reactor, and
   a diverter arranged below the heat exchanger and below the mixing chamber for diverting the reaction medium flowing downward through the mixing chamber in such a way that the reaction medium once again flows upward through the heat exchanger,
   wherein
   a region surrounding the heat exchanger tubes is in fluid connection with the first inlet,
   an inner region of the heat exchanger tubes forms part of the reaction space and is in fluid connection with the driving jet nozzle and the second outlet, and
   the apparatus is suitable for a continuous reaction of the liquid reactant with the gaseous reactant.

2. The apparatus according to claim 1, wherein the heat exchanger tubes are arranged in a bundle of tubes.

3. The apparatus according to claim 1, wherein the diverter is a diversion pan.

4. The apparatus according claim 1, wherein a third outlet for taking the reaction medium off from an internal circulatory flow is located above the heat exchanger.

5. The apparatus according to claim 1, wherein the mixing chamber is formed by plug-in tubes.

6. The apparatus according to claim 1, wherein the second inlet is installed below the heat exchanger and above the diverter.

7. The apparatus according to claim 6, wherein a further inlet for introducing the gaseous reactant into the reaction space is additionally provided above the heat exchanger.

8. The apparatus according to claim 1, wherein the mixing chamber is connected to a diffuser at a lower end of the mixing chamber.

9. The apparatus according to claim 1, wherein
   the apparatus comprises an ejector arranged from top downward in a longitudinal direction of the reactor,
   the ejector is formed by the driving jet nozzle, the mixing chamber, optionally a diffuser and optionally further cylindrical sections, and
   the ejector comprises at least three sections below the driving jet nozzle: an upper section which has an essentially round cross section having a diameter d1, a middle section which comprises the diffuser and whose cross section widens compared to the upper section from top downward, and a lower section which has an essentially round cross section having a diameter d2, which is larger than d1.

10. The apparatus according to claim 9, wherein a plurality of ejectors are used.

11. The apparatus according to claim 1, wherein a multiorifice nozzle is used as the driving jet nozzle.

12. The apparatus according to claim 1, wherein at least one third inlet is provided for the driving jet nozzle.

13. The apparatus according to claim 1, wherein an external circuit produces a fluid connection between the second outlet and the driving jet nozzle.

14. The apparatus according to claim 13, wherein a pump is arranged in the external circuit.

15. A process comprising:
continuously reacting a liquid reactant with a gaseous reactant in the apparatus according to claim 1, thereby obtaining a reaction product.

16. The process according to claim 15, wherein
the reaction medium flows through the heat exchanger tubes, and
the cooling medium surrounds the heat exchanger tubes.

17. The process according to claim 15, wherein said reacting is carried out in the presence of a suspended or dissolved catalyst.

18. The process according claim 17, wherein the catalyst is suspended in the reaction medium and is retained in an external circuit via crossflow filtration.

19. The process according to claim 15, wherein
the liquid reactant is a nitroaromatic, and
the gaseous reactant is hydrogen.

20. The process according to claim 15, wherein an internal circulatory flow is driven by the driving jet nozzle.

21. The process according to claim 15, wherein the reaction product is taken off from an external circuit.

\* \* \* \* \*